United States Patent [19]
Campbell et al.

[11] Patent Number: 5,458,572
[45] Date of Patent: Oct. 17, 1995

[54] CATHETER WITH BALLOON FOLDING INTO PREDETERMINED CONFIGURATIONS AND METHOD OF MANUFACTURE

[75] Inventors: Andrew J. Campbell, Reading; Daniel J. Kalashian, Watertown; David A. Ferrera, Lunenburg; George Michaels, Westford, all of Mass.

[73] Assignee: Boston Scientific Corp., Natick, Mass.

[21] Appl. No.: 270,144

[22] Filed: Jul. 1, 1994

[51] Int. Cl.⁶ .................................................. A61M 29/00
[52] U.S. Cl. ................................................ 604/96; 606/194
[58] Field of Search ........................... 604/96, 97, 100, 604/101, 280, 282; 606/191–194

[56] References Cited

U.S. PATENT DOCUMENTS

| | | | |
|---|---|---|---|
| 4,796,629 | 1/1989 | Grayzel | 604/96 X |
| 5,226,887 | 7/1993 | Farr et al. | 604/96 |
| 5,295,995 | 3/1994 | Kleiman | 606/194 |
| 5,318,587 | 6/1994 | Davey | 604/96 X |
| 5,320,634 | 6/1994 | Vigil et al. | 604/96 X |

*Primary Examiner*—John D. Yasko

[57] ABSTRACT

A medical catheter (10) having a balloon (3) adapted to be folded into a predetermined configuration. The catheter comprises a flexible inflation member (2) with a balloon (3) disposed on the inflation member (2). The balloon has a flexible wall defining an inflation chamber and the inflation chamber is in fluid flow relation with an inflation lumen in the inflation member. The balloon (3) is adapted for inflation from a folded configuration to an inflated, expanded configuration and back to the folded configuration. An array of longitudinally and circumferentially arranged ribs (6) is disposed in said wall (3a). The ribs (6) are either more stiff or less stiff than the wall (3a) whereby upon evacuation of inflation fluid from the balloon (3) either portions of the wall between the ribs will collapse between the ribs or the ribs will collapse within the wall.

15 Claims, 1 Drawing Sheet

CATHETER WITH BALLOON FOLDING INTO PREDETERMINED CONFIGURATIONS AND METHOD OF MANUFACTURE

BACKGROUND OF THE INVENTION

Balloon catheters are well known devices in which the catheter carries an inflatable balloon to occlude and seal a body space, to expand a blood vessel through pressurized inflation of the balloon or for other desired purposes which may typically be therapeutic procedures in the medical field.

An important characteristic of a dilation balloon catheter used for angioplasty is its profile, that is the outer diameter of the balloon when deflated. A low profile balloon is quite important and is usually attained by minimizing the dimensions of the core or inner tube where it extends through the balloon and by reducing the wall thickness of the balloon. The outer diameter effects the ease and ability of the dilation catheter to pass through a guide catheter through the coronary arteries and across a tight lesion. To reduce the outer diameter of the balloon in its deflated condition it is common to fold the balloon flat so that two wings or flaps are formed. These wings are then brought together so as to reduce the overall diameter of the deflated balloon. Commonly such configurations are achieved by installing a sleeve or balloon protector around the deflated balloon to bring the folds together. When inflation fluid is supplied to the folded balloon it causes the wings to unwrap so the balloon can inflate to its fully inflated configuration.

While reduction of profile is desirable it is also important to provide an inflated outer diameter of the balloon which is as large as possible relative to the deflated profile. When two wings are formed as the balloon is deflated they can be folded together to squeeze out the space between them without damaging the catheter during the procedure.

Commonly the wings of a balloon are folded or wrapped so they will return to a predetermined configuration when the balloon is deflated. Subsequent to inflation in an angioplasty procedure they will return to the formed configuration to enable easy withdrawal of the balloon from within the artery being treated. Reliance upon hand folded wings, however, can be fairly problematical because these wings do not necessarily conform to their original configuration upon deflation when they do not conform they may present a profile which is larger then necessary thereby possibly damaging the artery in which the catheter is inserted. Moreover when a catheter has to cross over several lesions or be used in several sites in the same procedure as in the case of a multi-vessel angioplasty, if the wings do not return to the predetermined configuration after evacuation of the inflation fluid the resultant deflated profile may compromise the ability to negotiate such vessels (or lesions). Moreover, abrasion can be increased together with the possible introduction of pin holes or wear spots.

The catheters for the medical procedure must be strong enough to withstand significant inflation pressures. They tend to be fairly stiff since the wall thickness must be sufficient to provide the necessary strength for these high pressures. Therefore when they are deflated, even if predetermined configurations are not introduced, they can flatten and lateral flat portions of the deflated balloon project laterally outwardly well beyond the rest of the catheter. It is undesirable to use balloons that have large, flat wings which may damage the artery wall as a deflated balloon is advanced through the arterial system into the desired position for inflation. Such flat wings can also interfere with the manipulation of the catheter and its easy advancement through the arterial system.

SUMMARY OF THE INVENTION

According to the present invention we have discovered a medical catheter having a balloon which can be folded into a predetermined configuration. The balloon includes a flexible wall which, when inflated, has a generally cylindrical shape and defines an inflation chamber. The inflation chamber is in fluid flow relation with an inflation lumen disposed within a catheter shaft. The balloon can be inflated from a folded configuration to an inflated, expanded configuration and upon evacuation of the inflation media, back to the folded configuration. Evacuation of the inflation media causes the balloon to revert to the predetermined configuration which has a low profile and will not excessively engage the walls of the artery by presenting excessively large wings. The wall of the balloon of the present invention has an array of circumferentially arranged ribs disposed therein. Webs are disposed between the ribs. The ribs are either more stiff or less stiff than the webs so upon deflation of the balloon either the webs will collapse about the ribs or the ribs will collapse between the webs. The ribs are formed of a plastic material disposed in lumens that are formed within the wall of the balloon, preferably by co-extrusion of the wall and ribs. The lumens are arranged predetermined locations relative to each other and extend from the distal end of the balloon to the proximal end. The ribs preferably are of a plastic material that is dissimilar (at least in stiffness) to the plastic material that is used to form the wall of the balloon or multiple sets of lumens of dissimilar material can be used within the balloon wall. In addition we have found that longitudinally disposed, circumferentially arranged ribs aid in the inhibition of balloon failures. If a ribbed balloon begins to tear circumferentially, the tear will be redirected along a rib we have found. When failure of balloons occurs, longitudinal tears are preferable since circumferential tearing can allow an entire portion of the failed balloon to remain in the patient which is highly undesirable.

DESCRIPTION OF THE PREFERRED EMBODIMENT

Figure 1:
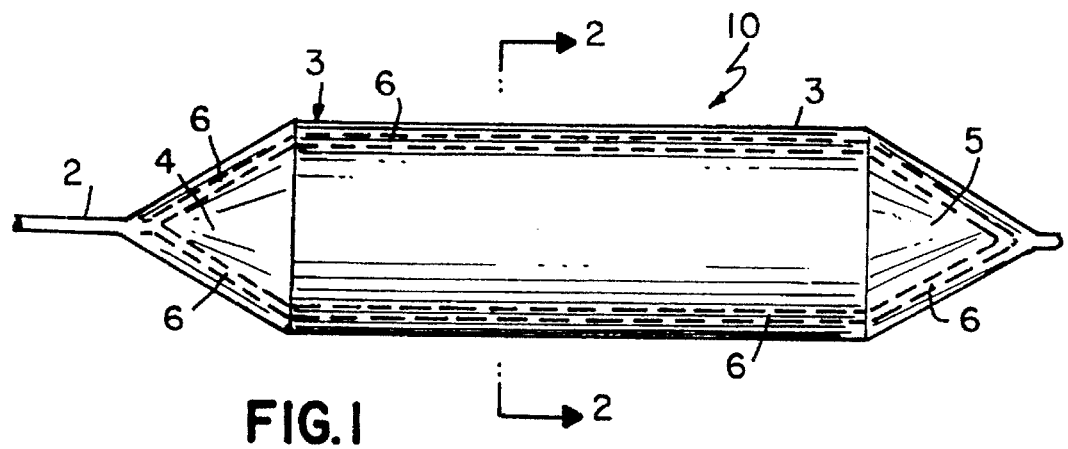
FIG. 1 is a side elevational view of a balloon catheter according to the present invention.

A balloon according to the present invention includes an inflation chamber formed by a balloon wall. The balloon wall is fabricated by co-extruding a hollow tube of two or more polymeric materials having dissimilar flexure characteristics using conventional extrusion techniques. A discrete phase, that is the phase which serves as the basis for the mechanical members or ribs dictates their locations and shapes. Materials that can be used for the discrete phase according to the present invention are engineering thermoplastics, polyolefins and thermoplastic elastomers. They include thermoplastic elastomers such as the melt processable rubbers and engineering thermoplastic elastomers, the latter comprising polyether ester, polyester ester, polyether block amides and styrene—butadiene block elastomers. The principal criteria for selection of materials is that they exhibit a difference in flexibility so that one phase is more flexible relative to the other phase. Preferably the balloons are formed of a high strength material such as high density polyethylene, Nylon, low density polyethylene, polyethylene copolymers, polyethylene terephthalate (PET), preferably biaxially oriented PET, polypropylene (PP), and other non-compliant engineering resins such as liquid crystalline polymer (LCP). Other materials that can be used are polyethylene (PE), particularly biaxially oriented PE (irradiated), polyvinyl chloride (PVC), and other compliant polymers. All of these plastic material are known to be suitable for medical balloon applications. A continuous phase, that is the phase that will form the balloon's wall (with the discrete phase enclosed within the wall) can be formed of polyethylene terephthalate or high or low density polyethylene. High density polyethylene and low density polyethylene copolymers can be extruded within polyethylene terephthalate. Nylon can be extruded within a high or low density polyethylene.

TABLE I

Exemplary of the flexural modulus per ASTM D790 @ 73° C. are as follows:

| Polyamide (Nylon 11) | 150 psi |
| LCP (Liquid Crystalline Polymer) | 1890 psi |
| Polyethylene | 185 psi |
| Polyimide | 475 psi |
| PPS (Polyphenylene Sulfide) | 550 psi |
| Polypropylene | 210 psi |
| PET | 400 psi |

TABLE II

Relative Stiffness of Materials Compared With PET

| MATERIAL | PERCENT INCREASE IN STIFFNESS |
| --- | --- |
| PET vs. Polyamide | 37.5% |
| PET vs. LCP | 472% |
| PET vs. P.E. | 46.75% |
| PET vs. Polyimide | 18.75% |
| PET vs. Polypropylene | 52.5% |

After the phases are co-extruded the discrete phases will be disposed within the continuous phase in lumens in the continuous phase. Each of the lumens which houses the discrete phases is disposed in a predetermined location relative to another lumen to provide a balloon with the smallest possible profile upon evacuation of inflation fluids. Preferably at least three or four lumens are circumferentially disposed in an array in which the lumens are equidistantly spaced from each other. More than six lumens generally is not satisfactory because of the bulk that they provide to the balloon.

Co-extrusion of multiple plastic materials is well known and conventional techniques are used for such processes. In the present invention materials are selected so that either the discrete phase is more stiff than the continuous phase or alternatively that the continuous is more stiff than the discrete phase. In the case where the discrete phase is more stiff than the continuous phase the continuous phase will form ribs which will extend through the entire length of the balloon and the webs between these ribs are less stiff than the ribs. Thus upon evacuation of the balloon the webs will collapse inwardly between the ribs and a predetermined configuration of the balloon will be formed. On the other hand the ribs can be less stiff than the balloon material. In that case the ribs will collapse inwardly between the ribs upon deflation and again a predetermined configuration of the balloon will be formed. The configuration can be such that the profile of the deflated balloon is the smallest that it can possibly be.

Following the fabrication of the balloon the discrete phase is left within the continuous phase and the extrusion is heated in the area where the balloon is to be formed to a temperature sufficient to soften the balloon in that area to permit stretching of the balloon wall. The extrusion is then pressurized to expand to the balloon to the desired diameter.

A catheter utilizing the herein-described balloon may be similar to any conventional balloon catheter assembly, with the herein-described novel balloon substituted for the conventional balloon. The catheter includes a shaft, and the proximal end of the balloon typically is joined to the shaft at the shaft distal end. The length of the catheter is sufficient to be threaded through the bodily cavity or cavities to the area to be treated with a sufficient length remaining outside the body to permit manipulation of the catheter. The shaft includes at least one internal lumen for inflating the balloon with an inflation fluid. Typically, a guidewire extends through the balloon, and may extend distally from the balloon. Alternatively, a wire may extend proximally through the shaft (via an additional lumen) to provide greater stiffness and strength to the shaft.

The catheter may be fabricated by conventional means by joining of the balloon to the catheter at the balloon's proximal and distal ends. The proximal joint may be accomplished by adhering the balloon's ends to the shaft. Heat sealing and/or adhesive are suitable for this joining process. An improved seal may be achieved by adhering the balloon to the shaft, slipping a flexible polymeric sleeve cover over the shaft with its distal end overlapping the balloon end, then adhering the sleeve cover to balloon and the shaft. Similar joining methods may be used to anchor the proximal end of the balloon to, for example, the guidewire.

Referring now to FIG. 1 a catheter 10 is shown the catheter 10 includes a flexible insertion member 2, a balloon 3, and a hollow shaft 2 of polymeric material, as is conventional in the art. The flexible insertion member 2 has at least one lumen for the delivery of an inflation media. The balloon 3 includes a proximal end member 4 and a distal end member 5. The proximal and distal end members can have a generally conical or hemispherical shape when inflated. An array of longitudinally extending, continuous lumens 6 is disposed within the proximal end member 4, the distal end member 5 and the body of the balloon 3. The lumens 6 extend from the distal end 5 of the balloon 3 to the proximal end 4. The number of lumens in the array can be varied as desired, three making a generally triangular shaped deflated balloon and four making a generally square shaped balloon, for example. As mentioned above each of the lumens 6 is filled with a plastic material which is either less stiff than the plastic material forming the balloon 3 or more stiff than it.

In the case where the plastic material filling the lumen 6 is more stiff than the material forming the balloon 3, the lumens 6 will form ribs which provide a structure that the wall 3 of the balloon will collapse inwardly around. In the case where the lumen is filled with a plastic that is less stiff than the plastic material forming the balloon 3 the lumen 6 will collapse inwardly toward the axis of the balloon again to form a balloon of minimum profile.

Figure 2A:
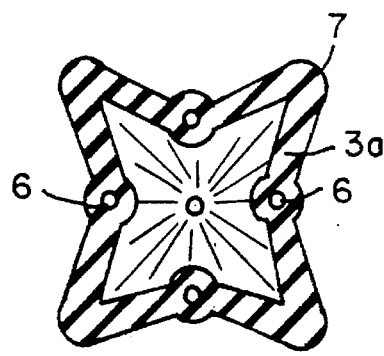
FIGS. 2A and 2B are cross-sectional views taken along the line II—II of FIG. 1 and showing two embodiments of constructions of the collapsible balloon according to the present invention.
Figure 2B:
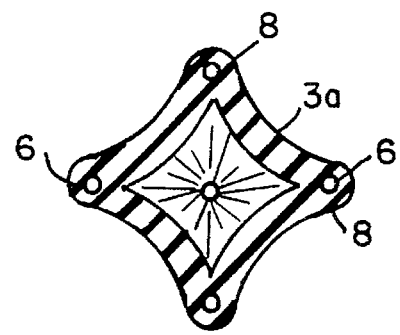

Referring to FIGS. 2A and 2B two embodiments are shown. With the embodiment of FIG. 2A the plastic material in the lumen 6 is more flexible than the plastic in the wall 3a. The thickness of wall 3a can be between about 0.0004" and 0.005". While a single layer of plastics material is shown to make the wall 3a it is also conventional in the art to co-extrude multi-layered walls in which case the lumen 6 can be co-extruded in either of the two layers or between two layers. In the embodiment shown in FIG. 2A the plastic material in the lumen 6 is less stiff than the plastic material of the wall 3a. Thus upon evacuation of the balloon the lumen 6 will move inwardly toward the axis of the balloon and wings 7 (without a lumen) will point outwardly from the axis. In the embodiment shown four lumens are utilized thereby giving a generally square configuration to the cross-section. In the embodiment shown in FIG. 2B the lumen 6 has a plastic material which is stiffer than the plastic material in the wall 3a thus the wings 8 will provide a bridge-like support for the webs between adjacent wings 8. Again this embodiment four lumens are used to house the more stiff plastic.

With regard to the stiffness we have found that phase should be at least 15% more stiff then the other phase to provide the benefits of the present invention. As mentioned previously the plastic in the lumen can be stiffer than the plastic of the web or visa versa.

Figure 3A:
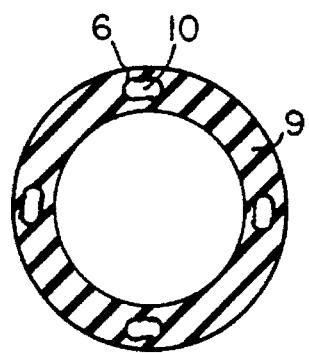
FIGS. 3A and 3B are cross-sectional views showing to differently-shaped lumens in a balloon tube extrusion. In one embodiment the lumen has an ovoid shape and in the other embodiment the lumen has a circular shape.
Figure 3B:
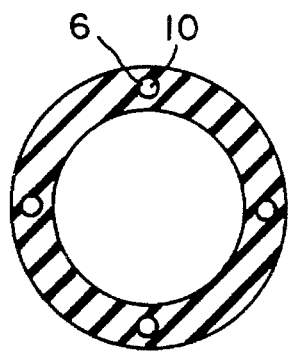

Referring to FIGS. 3A and 3B a co-extruded tube prior to balloon making is shown. The continuous portion 9 of the extrusion has four discrete portions 10 disposed within it in a circumferential array. In the embodiment shown FIG. 3A the discrete portion is disposed in a generally oval-shaped lumen. In the embodiment shown in FIG. 3A the discrete phase 10 is disposed within a generally circular lumen 6. Lumens of other cross sectional shapes can be used also. We have found that the lumens should be between 2 and 50% of the wall thickness. They are filled with plastic material forming the ribs to attain the desired objects of the present invention.

While it is apparent that modifications and changes can be made within the spirit and scope of the present invention, it is our intention, however, only to be limited by the scope of the appended claims.

As our invention, we claim.
What is claimed is:

1. A medical catheter having a balloon adapted to be folded into a predetermined configuration, said catheter comprising:

a flexible inflation member;

a balloon disposed on said inflation member, said balloon having a flexible wall defining an inflation chamber, said inflation chamber being in fluid flow relation with an inflation lumen in said inflation member, said balloon being adapted for inflation from a folded configuration to an inflated, expanded configuration and back to said folded configuration;

an array of longitudinally and circumferentially arranged ribs disposed in said wall, said ribs being either more stiff or less stiff than said wall whereby upon evacuation of inflation fluid from said balloon either portions of said wall between said ribs will collapse between said ribs or the ribs will collapse within said wall.

2. The medical catheter according to claim 1 wherein said ribs are 15% stiffer than said web or vice versa.

3. The medical catheter according to claim 1 wherein said rib or said web is formed of polyethylene terephthalate.

4. The medical catheter according to claim 1 wherein there are at least three ribs disposed in said balloon.

5. The medical catheter according to claim 4 wherein there are less than seven ribs in said balloon.

6. The medical catheter according to claim 1 wherein the thickness of the web is between about 0.0004 and 0.005".

7. The medical catheter according to claim 1 wherein the lumens are between about 2 and 50% of the wall thickness.

8. A medical catheter having a balloon adapted to be folded into a predetermined configuration, said catheter comprising:

a flexible inflation member;

a balloon disposed on said inflation member, said balloon having a flexible wall defining an inflation chamber and having a proximal and a distal end, said inflation chamber being in fluid flow relation with an inflation lumen in said inflation member, said balloon being adapted for inflation from a folded configuration to an inflated, expanded configuration and back to said folded configuration;

an array of longitudinally extending lumens disposed in said wall, said lumens being in predetermined locations relative to each other and extending between said distal and proximal end;

a rib of plastic material disposed in each of said lumens, said ribs being either more stiff or less stiff than said wall whereby upon evacuation of said inflation chamber either said wall will collapse about said ribs or said ribs will collapse between said wall.

9. The medical catheter according to claim 8 wherein said ribs are 15% stiffer than said web or vice versa.

10. The medical catheter according to claim 8 wherein said rib or said web is formed of polyethylene terephthalate.

11. The medical catheter according to claim 8 wherein there are at least three ribs disposed in said balloon.

12. The medical catheter according to claim 11 wherein there are less than seven ribs in said balloon.

13. The medical catheter according to claim 8 wherein the thickness of the web is between about 0.0004 and 0.005".

14. The medical catheter according to claim 8 wherein the lumens are between about 2 and 50% of the wall thickness.

15. A method of constructing a medical balloon wherein the balloon preferably fails with a tear substantially parallel to the axis of the balloon rather than normal to the axis, said method comprising:

disposing a balloon on an inflation member, said balloon having a flexible wall defining an inflation chamber, said inflation chamber being in fluid flow relation with an inflation lumen in said inflation member, said balloon being adapted for inflation from a folded configuration to an inflated, expanded configuration and back to said folded configuration said balloon further having an array of longitudinally and circumferentially arranged ribs disposed in said wall, said ribs being either more stiff or less stiff than said wall whereby upon evacuation of inflation fluid from said balloon either portions of said wall between said ribs will collapse between said ribs or the ribs will collapse within said wall.

* * * * *